United States Patent [19]

Rizkalla et al.

[11] 4,058,542
[45] Nov. 15, 1977

[54] CONVERSION OF THALLIUM (I) TO THALLIUM (III)

[75] Inventors: Nabil Rizkalla, River Vale; Anthony N. Naglieri, Pine Brook, both of N.J.

[73] Assignee: Halcon International, Inc., New York, N.Y.

[21] Appl. No.: 740,148

[22] Filed: Nov. 8, 1976

[51] Int. Cl.$^2$ .............................................. C01G 15/00
[52] U.S. Cl. ................................ 260/429 R; 423/111; 423/122; 423/123
[58] Field of Search ............... 423/111, 122, 123, 495, 423/124; 260/429 R

[56] References Cited

FOREIGN PATENT DOCUMENTS 764,330  8/1967  Canada ............................... 423/111

OTHER PUBLICATIONS

Z. Anorg. Chem., vol. 44, pp. 379, 399–405.

Primary Examiner—Edward Stern
Attorney, Agent, or Firm—William C. Long; David Dick; Riggs T. Stewart

[57] ABSTRACT

A monovalent thallium compound is converted to a trivalent thallium compound by treating the thallium (I) compound with molecular oxygen in the presence of a Group VIII noble metal catalyst and in the presence of a promoter comprising a heterocyclic tertiary amine to oxidize the thallium (I) compound to a thallium (III) compound.

5 Claims, No Drawings

CONVERSION OF THALLIUM (I) TO THALLIUM (III)

This invention relates to the oxidation of thallium (I) to thallium (III).

Trivalent thallium compounds, i.e., thallic compounds, have been used as oxidizing agents in various reactions. For example, Kruse et al, J. Org. Chem. 36, 1154 (1971) describe the epoxidation of certain olefins with thallic acetate and Kruse U.S. Pat. No. 3,641,067 relates to the preparation of the epoxides of propylene and isobutylene by means of lower thallic alkanoates.

In all of these reactions the trivalent thallium is reduced to the monovalent state and, if the thallium is to be reused in the reaction, it is necessary to reoxidize or "regenerate" it by converting thallium (I) to thallium (III). Various methods for effecting this conversion have been proposed and are more or less effective. Thus, Hirose et al U.S. Pat. No. 3,399,956 describes the oxidation of Tl(I) to Tl(III) by means of molecular oxygen in an acidic aqueous medium containing chloride or bromide ions and an ion of a redox metal such as copper, mercury, chromium, manganese, iron, cobalt, and nickel. Hirose et al refer to earlier processes for effecting the conversion of Tl(I) to Tl(III) and point out the problems involved in achieving the desired oxidation and the disadvantages and drawbacks of prior procedures. While the Hirose et al process is described as an improvement over processes previously proposed, it is limited to the use of aqueous chloride or bromide solutions so that the thallium (III) is always produced as a chloride or bromide and it is generally necessary to use the redox metal in large amounts in relation to the thallium compound being treated. It is proposed to convert thallium (I) to thallium (III) in the application of William Brill, Ser. No. 740,143 entitled "Catalytic Conversion of Thallium (I) to Thallium (III)" by means of molecular oxygen using a Group VIII noble metal as a catalyst but, in the absence of a promoter, an equilibrium appears to be reached when about 50 mol % of the thallium (I) has been converted to thallium (III), and further conversion tends not to occur. Said application is being filed on even date herewith.

It is an object of this invention to provide a process for converting thallium (I) to thallium (III) which makes possible high conversions.

In accordance with the invention, a monovalent thallium compound is converted to a trivalent thallium compound by treating the thallium (I) compound with molecular oxygen in the presence of a Group VIII noble metal catalyst and in the presence of a promoter for the catalyst in a fluid medium to oxidize the thallium (I) compound to achieve high conversions to thallium (III) in a rapid and efficient manner. Conversions well above 50% are readily obtained.

The Group VIII noble metals comprise platinum, palladium, rhodium, ruthenium, osmium and iridium, but platinum, palladium, ruthenium and rhodium are preferred, especially platinum and palladium. Mixed catalysts can be used if desired. The catalyst is preferably used in a heterogenous system, e.g., in the form of a suspension in the reaction medium and in this case the catalyst is ordinarily supported upon a solid carrier. Thus, the Group VIII noble metal catalyst may be suitably added as a compound of the above-mentioned metals, e.g., an oxide, preferably on a carrier, but it is most preferred to add the catalyst as the finely-divided metal, e.g., platinum black, or as the metal supported on a carrier.

When the Group VIII noble metal catalyst is supported upon a carrier, the carrier or substrate which is employed is suitably in the form of a porous solid of such size that it can be readily dispersed in the liquid reaction medium, e.g., from 400 mesh/inch to ¼-inch particle sizes. Such carrier materials are exemplified by pumice, alumina, silica, silica-alumina, magnesia, diatomaceous earth, bauxite, titania, zirconia, clays, both natural and acid treated such as Super-Filtrols, attapulgus (attapulgite), lime, magnesium silicate, silicon carbide, activated and unactivated carbons, zeolites as well as the zeolitic molecular sieves, solid foams, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in Schultz U.S. Pat. No. 3,717,670 in connection with rhodium compounds and, indeed, many such supported catalysts are available commercially, particularly in the case of the zero valent free metal.

Concentrations of the Group VIII noble metal component on the support can vary widely but illustrative concentrations lie within the range of 0.1 to 20 wt. %. Higher concentrations may, however, be used if desired.

The ratio of catalyst to monovalent thallium compound can also vary over a wide range. For example, 0.1 to 40 mols of catalyst per 100 mols of monovalent thallium compound are advantageously used, but lesser or greater amounts may be employed, if desired, the upper limit being determined only by economic considerations and the lower limit only by the amount which will be catalytically effective. In any case, only catalytic quantities are required to bring about a rapid conversion.

The promoter for the Group VIII noble metal catalyst in accordance with the invention is a heterocyclic tertiary amine which may contain one or more nitrogen atoms and one or more rings. Examples of amines of the character indicated which are normally liquid at room temperatures include pyridine, the alkyl-substituted pyridines, such as the picolines, the lutidines and the like, quinoline, lepidine, quinaldine and other alkyl-substituted quinolines, isoquinoline and alkyl-substituted iso-quinolines, pyrimidine, pyridazine, alkyl N-substituted heterocyclic secondary amines such as N-methyl imidazole, N-methyl piperidine, the N-methyl pipecolines, N-methyl pyrrolidine, N-methyltriazole, and the like. The alkyl substituents preferably are lower alkyl, i.e., 1 to 5 carbon atoms. Higher-melting heterocyclic amines and heterocyclic tertiary amines which are substituted by groups other than alkyl such as hydroxy, halo, alkoxy, and like groups which are non-reactive in the system are also suitably used. Examples of such promoters are hydroxy pyridines, e.g., 2-hydroxypyridine, bipyridine, e.g., 2,2-bipyridine, chloropyridines such as 2-chloropyridine and like halo-substituted pyridines and quinolines, 4-methoxypyridine and like alkoxy pyridines and quinolines, 2-phenyl pyridine and like phenylsubstituted pyridines and quinolines, pyrazine, phenanthridine, phthalazine, quinazoline, quinoxaline, cinnoline, isoxazole, N-methyl indole, and the like. It is to be understood, however, that the foregoing named heterocyclic amines are given for illustrative purposes only.

The amount of promoter should ordinarily be at least 0.1 mol per mol of thallium (I) compound being treated, preferably at least 1 mol per mol. The upper limit is not critical and may, for example, be 500 mols of promoter per mol of thallium (I) compound or more. The upper limit is determined only by practical economic considerations.

Ordinarily, the higher the reaction temperature, the greater the reaction rate. It is unnecessary, however, to employ high temperatures. Normally, the reaction temperature may range from 10° to about 200° C. Typically, temperatures of 60° to 160° C are used, but higher or lower temperatures are operable. Excessively high temperatures, however, are not advantageous because they may eventually result in reaction between the thallium compounds and the solvent. Total pressure is not a specific parameter of the process and atmospheric or superatmospheric pressures may be employed but, desirably, oxygen partial pressures above the reaction mixture of at least 20 psi, preferably 200 to 2000 psi are provided and higher oxygen partial pressures, e.g., up to 10,000 psi can be used, if desired. It is generally desirable to stir the reaction medium, particularly when a heterogenous catalyst is employed, and this may be effected by mechanical agitation, shaking, and like means known to the art.

Any convenient monovalent thallium compound can be treated in accordance with the invention. Typically, the compound will be a salt which may be organic, such as a carboxylate of an alkyl, cycloalkyl or aryl carboxylic acid containing up to 20 carbon atoms, such as an acetate or benzoate, or inorganic, such as a nitrate, a sulfate, or a halide, but other compounds may be used, such as hydroxides, if desired. The thallous compound is suitably one which is at least partly soluble in the liquid medium employed.

The thallous compounds resulting from the epoxidation reactions described in the above-mentioned Kruse et al article and Kruse patent will be carboxylates and it is a feature of this invention that such thallous carboxylates can be converted to the thallic carboxylates with ease so that the conversion products can be recycled to the epoxidation reaction.

The reaction medium for the conversion of monovalent thallium to trivalent thallium can be aqueous or non-aqueous. Non-aqueous media comprise organic solvents of various types as are well known to the art, including polar and nonpolar solvents, but the polar solvents are particularly preferred. Typical polar organic solvents include the carboxylic acids such as acetic acid, ethers such as tetrahydrofuran and p-dioxane, tertiary alcohols such as t-butyl alcohol, ether alcohols such as polyglycols, aliphatic nitriles such as acetonitrile and propionitrile, amides such as dimethyl formamide and dimethyl acetamide, ketones such as acetone, methyl ethyl ketone and diethylketone, polar chlorinated hydrocarbons such as chloroform, as well as dimethyl sulfoxide, and the like, glycol ethers such as diethylene glycol, ethylene glycol, ethylene glycol dimethyl ether, ethylene glycol diethyl ether, and diethylene glycol diethyl ether, glycol esters such as ethylene glycol diacetate, diethylene glycol diacetate, and the corresponding ethers and esters of propylene glycol, butylene glycol, and the like. The normally liquid heterocyclic tertiary amines used as promoters in accordance with the invention, such as those previously named, can serve as solvents by themselves and no additional solvent is necessary but preferably they are used in combination with a solvent of the type mentioned above. Non-polar solvents include the hydrocarbons and chlorinated hydrocarbons such as carbontetrachloride. It will be understood that a solvent is preferably chosen which is not susceptible to oxidation under the particular conditions selected for the oxidation.

While an organic solvent can be used as the sole solvent component, in addition to the heterocyclic amine promoter, a water-polar organic solvent mixture containing up to about 50 volume percent water, typically about 5–10% water, can also be used. When water is present, and acids are absent, the trivalent thallium produced will normally be converted into the hydroxide which will precipitate and can be readily recovered and converted into any desired thallic salt in conventional manner, e.g., the hydroxide can be converted to a thallic salt by reaction with the appropriate acid. Therefore, an acid providing an anion to combine with all of the thallium (III) formed should be present.

If an anion corresponding to the anion of the thallous compound is present, then the thallic compound will be obtained in the form of a salt containing that anion. On the other hand, other thallic salts can be formed by supplying the appropriate anion, e.g., by adding a different carboxylic acid to the reaction mixture. For example, if the monovalent thallium is in the form of an acetate, then acetic acid is advantageously included in the reaction mixture so that all of the trivalent thallium will also be obtained in the form of the acetate. Sufficient acetic acid is, of course, present to provide the necessary molecular quantity. Similarly, if a propionate is desired, then propionic acid is added to the reaction medium. As previously indicated, the carboxylic acid can also serve as a solvent. The thallium (III) compound can thus be obtained in various forms as desired and, as mentioned, it can be in the same form as the thallium (I) compound supplied.

Thus, monovalent thallium compounds can be readily converted to trivalent thallium compounds, and the reaction medium containing the trivalent thallium compound produced can be used directly or after suitable treatment, such as filtration to remove the solid noble metal catalyst, for epoxidation, or other reaction. The trivalent thallium compound can also be separated from the reaction medium by precipitation, evaporation of solvent, or the like, if desired.

The invention will be more fully understood by reference to the following examples of specific embodiments thereof, but it will be understood that these examples are given for illustrative purposes only and are not intended as limitative of the invention. In the Examples, determinations of the thallium (III) product were carried out by means of conventional complexiometric analyses using standard ethylene nitrilo tetraacetic acid. The reaction mixture is analyzed in each case at the end of the indicated reaction period.

EXAMPLE 1

Into a 200 cc stirred autoclave is charged a 0.1M solution of thallium (I) acetate in 3.7 volume percent acetic acid and 96.3 volume percent pyridine, along with 0.025 mol per liter of platinum supported on alumina, the support containing 5 percent by weight of the catalytic metal. The autocalve is pressured with molecular oxygen to 500 psig (25° C) and then heated at 80° C for 2 hours with continuous stirring. The autoclave is cooled, depressured, and the reaction mixture is analyzed and found to contain thallium (III) in an amount corresponding to a 70% conversion of thallium (I) to thallium (III). In this and the following examples the catalysts are commercially available products supplied by Chemical Division of Englehard Industries and/or the Alpha Products Division of the Ventron Corp. The stirred autoclave used in this example is also used as the reaction vessel in the following examples.

EXAMPLE 2

The autoclave is charged with a 0.1M solution of thallium (I) acetate in 90 volume percent acetic acid and 10 volume percent pyridine, along with 0.025 mol per liter of platinum supported on alumina, the support containing 5 percent by weight of the catalytic metal. The autoclave is pressured with molecular oxygen to 1000 psig (25° C) and then heated at 80° C for 4 hours with continuous stirring. The autoclave is cooled, depressured, and the reaction mixture is analyzed and found to contain thallium (III) in an amount corresponding to 68% conversion of thallium (I) to thallium (III).

EXAMPLE 3

The autoclave is charged with a 0.1M solution of thallium (I) acetate in 18 volume percent propionic acid, 77 volume percent tetrahydrofuran and 5 volume percent pyridine, along with 0.025 mol per liter of platinum supported on alumina, the support containing 5 percent by weight of the catalytic metal. The autoclave is pressured with molecular oxygen to 800 psig (25° C) and then heated at 80° C for 4 hours with continuous stirring. The autoclave is cooled, depressured, and the reaction mixture is analyzed and found to contain thallium (III) in an amount corresponding to a 90% conversion of thallium (I) to thallium (III).

EXAMPLE 4

The autoclave is charged with a 0.1M solution of thallium (I) acetate in 20 volume percent iso-butyric acid, 75 volume percent tetrahydrofuran and 5 volume percent pyridine, along with 0.025 mol per liter of platinum supported on alumina, the support containing 5 percent by weight of the catalytic metal. The autoclave is pressured with molecular oxygen to 800 psig (25° C) and then heated at 80° C for 3 hours with continuous stirring. The autoclave is cooled, depressured, and the reaction mixture is analyzed and found to contain thallium (III) in an amount corresponding to an 83% conversion of thallium (I) to thallium (III).

EXAMPLE 5

The autoclave is charged with a 0.1M solution of thallium (I) acetate in 18 volume percent propionic acid, 5 volume percent pyridine, 67 volume percent tetrahydrofuran and 10 volume percent water along with 0.025 mol per liter of platinum supported on alumina, the support containing 5 percent by weight of the catalytic metal. The autoclave is pressured with molecular oxygen to 800 psig (25° C) and then heated at 80°0 C for 3 hours with continuous stirring. The autoclave is cooled, depressured, and the reaction mixture is analyzed and found to contain thallium (III) in an amount corresponding to a 60% conversion of thallium (I) to thallium (III).

EXAMPLE 6

The autoclave is charged with a 0.1M solution of thallium (I) acetate in 18 volume percent acetic acid, 5 volume percent pyridine and 77 volume percent tetrahydrofuran, along with 0.025 mol per liter of platinum supported on alumina, the support containing 5 percent by weight of the catalytic metal. The autoclave is pressured with molecular oxygen to 1000 psig (25° C) and then heated at 80° C for 3 hours with continuous stirring. The autoclave is cooled, depressured, and the reaction mixture is analyzed and found to contain thallium (III) in an amount corresponding to a 80% conversion of thallium (I) to thallium (III).

EXAMPLE 7

Example 6 is repeated except that the tetrahydrofuran is replaced by pyridine, to give a liquid mixture of 18 volume percent propionic acid and 82 volume percent pyridine. A conversion to thallium (III) of 98% is realized.

EXAMPLE 8

Example 7 is repeated except that the reaction is carried out for four hours. A conversion of 98% is again obtained.

EXAMPLE 9

When Example 8 is repeated but the propionic acid is omitted so that the liquid medium is 100 volume percent pyridine, the conversion falls to 2%.

EXAMPLE 10

The autoclave is charged with a 0.1M solution of thallium (I) acetate in 18 volume percent propionic acid and 82 volume percent tetrahydrofuran along with 0.025 mol per liter of platinum supported on alumina, the support containing 5 percent by weight of the catalytic metal and an amount of 2,2-bipyridine equal in wt. to the supported catalyst. The autoclave is pressured with molecular oxygen to 800 psig (25° C) and then heated at 80° C for 2 hours with continuous stirring. The autoclave is cooled, depressured, and the reaction mixture is analyzed and found to contain thallium (III) in an amount corresponding to a 99% conversion of thallium (I) to thallium (III).

EXAMPLE 11

Example 10 is repeated except that an equal weight of 2-hydroxy pyridine is substituted for 2,2-bipyridine. A conversion to thallium (III) of 68% is realized.

EXAMPLE 12

The autoclave is charged with a 0.1M solution of thallium (I) acetate in 18 volume percent propionic acid, 77 volume percent tetrahydrofuran and 5 volume % 3-picoline, along with 0.025 mol per liter of platinum supported on alumina, the support containing 5 percent by weight of the catalytic metal. The autoclave is pressured with molecular oxygen to 800 psig (25° C) and then heated at 80° C for 2 hours with continuous stirring. The autoclave is cooled, depressured, and the reaction mixture is analyzed and found to contain thallium (III) in an amount corresponding to a 63% conversion of thallium (I) to thallium (III).

EXAMPLE 13

The autoclave is charged with a 0.1M solution of thallium (I) acetate in 18 volume percent propionic acid, 72 volume percent tetrahydrofuran and 10 volume percent N-methylimidazole, along with 0.025 mol per liter of platinum supported on alumina, the support containing 5 percent by weight of the catalytic metal. The reaction is carried out as described in Example 12. The reaction mixture is found to contain thallium (III) in an amount corresponding to a 99% conversion of thallium (I) to thallium (III).

EXAMPLE 14

The autoclave is charged with a 1M solution of thallium (I) acetate in 25 volume percent iso-butyric acid, 15 volume percent pyridine and 60 volume percent triglyme, along with 0.05 mol per liter of platinum supported on alumina, the support containing 10 percent by weight of the catalytic metal. The autoclave is pressured with molecular oxygen to 800 psig (25° C) and then heated at 80° C for 3 hours with continuous stirring. The autoclave is cooled, depressured, and the reaction mixture is analyzed and found to contain thallium (III) in an amount corresponding to a 70% conversion of thallium (I) to thallium (III).

EXAMPLE 15

The autoclave is charged with a 1M solution of thallium (I) acetate in 50 volume percent acetic acid, 20 volume percent pyridine and 30 volume percent ethylene glycol diacetate, along with 0.1 mol per liter of platinum supported on alumina, the support containing 10 percent by weight of the catalytic metal. The autoclave is pressured with molecular oxygen to 1000 psig (25° C) and then heated at 90° C for 2 hours with continuous stirring. The autoclave is cooled, depressured, and the reaction mixture is analyzed and found to contain thallium (III) in an amount corresponding to a 91.4% conversion of thallium (I) to thallium (III).

EXAMPLE 16

The autoclave is charged with a 0.1M solution of thallium (I) acetate in 50 volume percent propionic acid, 20 volume percent pyridine and 30 volume percent ethylene diacetate, along with 0.1 mol per liter of platinum supported on activated carbon, the support containing 10 percent by weight of the catalytic metal. The reaction is carried out as described in Example 15. The reaction mixture is found to contain thallium (III) in an amount corresponding to 71% conversion of thallium (I) to thallium (III).

Since it has been observed that in the absence of a promoter, an equilibrium appears to be reached when 50% of the thallium (I) has been converted to thallium (III), i.e., when there is an equal molar ratio between thallium (I) and thallium (III), and further conversion tends not to occur, a number of experiments were carried out with a charge of equal molar parts of monovalent and trivalent thallium salts in the presence of promoters in accordance with the invention and the following experiments further demonstrate that the promoters make possible further conversion of thallium (I) to thallium (III) above the 50% point.

EXAMPLE 17

The autoclave is charged with a solution of thallium (I) acetate and thallium (III) acetate each in 0.025M concentration in 18 volume percent propionic acid, 57 volume percent tetrahydrofuran and 25 volume percent pyridine, along with 0.5 mol per liter of platinum supported on alumina, the support containing 5 percent by weight of the catalytic metal. The autoclave is pressured with molecular oxygen to 800 psig (25° C) and then heated at 80° C for 3 hours with continuous stirring. The autoclave is cooled, depressured, and the reaction mixture is analyzed and found to contain thallium (III) in an amount corresponding to a 92% conversion of thallium (I) to thallium (III).

EXAMPLE 18

Example 17 is repeated except that there is used a solution of thallium (I) acetate and thallium (III) acetate each in 0.025M concentration in 18 volume percent propionic acid, 77 volume percent tetrahydrofuran and 5 volume percent pyridine. The reaction mixture is found to contain thallium (III) in an amount corresponding to an 80% conversion of thallium (I) to thallium (III).

EXAMPLE 19

The autoclave is charged with a solution of thallium (I) and thallium (III) acetates each in 0.5M concentration in 30 volume percent propionic acid and 70 volume percent pyridine, along with 0.1 mol per liter of platinum supported on alumina, the support containing 10 percent by weight of the catalytic metal. The autoclave is pressured with molecular oxygen to 1000 psig (25° C) and then heated at 90° C for 2 hours with continuous stirring. The autoclave is cooled, depressured, and the reaction mixture is analyzed and found to contain thallium (III) in an amount corresponding to 90% conversion of thallium (I) to thallium (III).

EXAMPLE 20

Example 19 is repeated except that the solution is composed of 70 volume percent propionic acid and 30 volume percent pyridine. A conversion of 90% to thallium (III) is realized.

EXAMPLE 21

Example 19 is again repeated except that the solution is composed of 56 volume percent propionic acid, 33 volume percent pyridine and 11 volume percent water. A conversion to thallium (III) of 92.4% is obtained.

EXAMPLE 22

Example 19 is once again repeated except that the solution in this experiment is composed of 50 volume percent propionic acid, 20 volume percent pyridine and 30 volume percent ethylene glycol diacetate. A conversion of thallium (I) to thallium (III) of more than 97% is realized.

EXAMPLE 23

Example 22 is repeated but a temperature of 110° C and a 1-hour reaction time are employed. A conversion thallium (I) to thallium (III) of 84.7% is obtained.

EXAMPLE 24

Example 22 is again repeated by a temperature of 123° C and a reaction time of 45 minutes are employed. The conversion of thallium (I) to thallium (III) is more than 93%.

EXAMPLE 25

Example 23 is repeated but the pressure is lowered to 600 psig. The conversion of thallium (I) to thallium (III) is found to be 80.6%.

EXAMPLE 26

Using the charge and pressure conditions of Example 22, the reaction is carried out at 140° C for 30 minutes. The conversion of thallium (I) to thallium (III) is found to be 80%.

EXAMPLE 27

In this example the procedure of Example 22 is employed using a charge composed of thallium (I) acetate and thallium (III) acetate each in 0.5M concentration in 44 volume percent pivalic acid, 16 volume percent pyridine and 40 volume percent ethylene glycol diacetate. The conversion of thallium (I) to thallium (III) is determined to be 87.6%.

EXAMPLE 28

The procedure of Example 22 is again employed using a charge composed of thallium (I) acetate and thallium (III) acetate each in 0.5M concentration in 50 volume percent acetic acid, 20% pyridine and 30% ethylene glycol diacetate. Conversion of thallium (I) to thallium (III) is 85.8%.

EXAMPLE 29

Again using the procedure of Example 22, but at 80° C and with a charge composed of thallium (I) and thallium (III) each in 0.5M concentration in 25 volume percent propionic acid, 60 volume percent pyridine and 15 volume percent triglyme, a conversion of thallium (I) to thallium (III) of more than 98% is realized.

EXAMPLE 30

The autoclave is charged with thallium (I) acetate and thallium (III) acetate each in 0.5M concentration in 25 volume percent propionic acid, 55 volume percent pyridine, 15 volume percent ethylene glycol diacetate and 5 volume percent water, along with 0.1 mol per liter of platinum supported on alumina, the support containing 10 percent by weight of the catalytic metal. The autoclave is pressured with molecular oxygen to 1000 psig (25° C) and then heated at 80° C for 4 hours with continuous stirring. After the autoclave has been cooled and depressured, the reaction mixture is analyzed and found to contain thallium (III) in an amount corresponding to more than 84% conversion of thallium (I) to thallium (III).

EXAMPLE 31

The autoclave is charged with thallium (I) acetate and thallium (III) acetate each in 0.5M concentration in 25 volume percent propionic acid, 60 volume percent pyridine and 15 volume percent triglyme, along with 0.1 mol per liter of platinum supported on alumina, the support containing 10 percent by weight of the catalytic metal. The reaction is carried out at 1000 psig as in Example 30 but at 60° C for 2 hours. The reaction mixture is found to contain thallium (III) in an amount corresponding to a 63.8% conversion of thallium (I) to thallium (III).

EXAMPLE 32

Example 29 is repeated but with 0.05M concentration of platinum on an alumina support containing 5 percent by weight of the catalytic material. A conversion of 79.8% is found to have occurred.

EXAMPLE 33

The autoclave is charged with thallium (I) acetate and thallium (III) acetate each in 0.5M concentration in 25 volume percent propionic acid, 60 volume percent tetrahydrofuran and 15 volume percent pyridine, along with 0.1 mol per liter of platinum supported on alumina, the support containing 10 percent by weight of the catalytic metal. The autoclave is pressured with molecular oxygen to 1000 psig (25° C) and then heated at 80° C for 4 hours with continuous stirring. After the autoclave has been cooled and depressured, the reaction mixture is found to contain thallium (III) in an amount corresponding to a 82.6% conversion of thallium (I) to thallium (III).

EXAMPLE 34

The autoclave is charged with thallium (I) acetate and thallium (III) acetate each in 0.5M concentration in 55 volume percent acetic acid, 35 volume percent ethylene glycol diacetate and 10 volume percent N-methylimidazole, along with 0.1 mol per liter of platinum supported on alumina, the support containing 10 percent by weight of the catalytic metal. The reaction is carried out as described in Example 28. The reaction mixture is found to contain thallium (III) in an amount corresponding to a 54.4% conversion of thallium (I) to thallium (III).

In the foregoing examples the thallium has been charged in the form of an acetate. The following examples illustrate the use of thallium salts, both organic and inorganic, other than alkanoic carboxylates.

EXAMPLE 35

The autoclave is charged with a 0.1M solution of thallium (I) benzoate in 50 volume percent propionic acid, 30 volume percent ethylene glycol diacetate and 20 volume percent pyridine, along with 0.1 mol per liter of platinum supported on alumina, the support containing 10 percent by weight of the catalytic metal. The autoclave is pressured with molecular oxygen to 1000 psig (25° C) and then heated at 110° C for 3 hours with continuous stirring. The autoclave is cooled, depressured, and the reaction mixture is analyzed and found to contain thallium (III) in an amount corresponding to a 100% conversion of thallium (I) to thallium (III).

EXAMPLE 36

The autoclave is charged with a 0.1M solution of cyclopentadienyl thallium (I) in 50 volume percent propionic acid, 30 volume percent ethylene glycol diacetate and 20 volume percent pyridine, along with 0.1 mol per liter of platinum supported on alumina, the support containing 10 percent by weight of the catalytic metal. The autoclave is pressured with molecular oxygen to 1000 psig (25° C) and then heated at 110° C for 2 hours with continuous stirring. The autoclave is cooled, depressured, and the reaction mixture is analyzed and found to contain thallium (III) in an amount corresponding to an 89% conversion of thallium (I) to thallium (III).

EXAMPLE 37

The autoclave is charged with 0.92M solution of thallous hydroxide in 50 volume percent propionic acid, 30 volume percent ethylene glycol diacetate and 20 volume percent pyridine, together with 0.1 mol per liter of platinum supported on alumina, the support containing 10 percent by weight of the catalytic metal. The autoclave is pressured with molecular oxygen to 1000 psig (25° C) and then heated at 80° C for 2 hours with continuous stirring. After the autoclave has been cooled and depressured, the reaction mixture is found to contain thallium (III) in an amount corresponding to a 89% conversion of thallium (I) to thallium (III).

EXAMPLE 38

The autoclave is charged with a 0.1M solution of thallous carbonate in 50 volume percent propionic acid, 30 volume percent ethylene glycol diacetate and 20 volume percent pyridine, together with 0.1 mol per liter of platinum supported on alumina, the support containing 10 percent by weight of the catalytic metal. The autoclave is pressured with molecular oxygen to 1000 psig (25° C) and then heated at 110° C for 3 hours with continuous stirring. The autoclave is cooled, depressured, and the reaction mixture is analyzed and found to contain thallium (III) in an amount corresponding to 98% conversion of thallium (I) to thallium (III).

EXAMPLE 39

The autoclave is charged with a 0.1M solution of thallous chloride in 50 volume percent propionic acid, 30 volume percent ethylene glycol diacetate and 20 volume percent pyridine, with 0.1 mol per liter of platinum supported on alumina, the support containing 10 percent by weight of the catalytic metal. The reaction is carried out as described in Example 38. The reaction mixture is found to contain thallium (III) in an amount corresponding to a 91% conversion of thallium (I) to thallium (III).

EXAMPLE 40

Example 39 is repeated but with the thallium (I) in the form of thallous nitrate. Analysis shows an 85% conversion of thallium (I) to thallium (III).

EXAMPLE 41

Example 39 is again repeated but with the thallium (I) in the form of thallous sulfate. A conversion of thallium (I) to thallium (III) of 88% is achieved.

What is claimed is:

1. A process for converting a thallium (I) compound to a thallium (III) compound which comprises reacting the thallium (I) compound in a liquid medium with molecular oxygen in the presence of a Group VIII noble metal and in the presence of a promoter comprising a heterocyclic tertiary amine.

2. A process as defined in claim 1, wherein the promoter comprises a pyridine.

3. A process as defined in claim 1, wherein the Group VIII noble metal is platinum or palladium.

4. A process as defined in claim 1, wherein the reaction is carried out under an oxygen partial pressure of 20 to 10,000 psi.

5. A process as defined in claim 1, wherein the thallium (I) compound is a thallium (I) carboxylate.

* * * * *